US00PP08071P

United States Patent [19]

Zaiger et al.

[11] Patent Number: Plant 8,071

[45] Date of Patent: Dec. 22, 1992

[54] PEACH TREE "COMPACT FLAVORETTE"

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 4005 California Ave., all of Modesto, Calif. 95351

[21] Appl. No.: 737,641

[22] Filed: Jul. 30, 1991

[51] Int. Cl.[5] ..... A01H 5/00

[52] U.S. Cl. ..... Plt./43.3

[58] Field of Search ..... Plt./43.2, 43.3

*Primary Examiner*—James R. Feyrer

[57] ABSTRACT

A new and distinct variety of peach tree with the unique combination of desirable features:

1. Semi-dwarf in size, approximately 60% of normal size.
2. Regular and heavy production of fruit.
3. Fruit with an attractive red skin color.
4. Fruit with good flavor and eating quality.
5. The fruit having firm flesh, good handling and shipping quality.
6. The fruit holding firm on the tree approximately 10 days after maturity.

1 Drawing Sheet

ORIGIN OF THE VARIETY

The present new variety of semi-dwarf peach tree was developed and grown in our experimental orchard located near Modesto, Calif. from a second generation cross between a low chilling peach seedling of unknown parentage and Amparo Peach (U.S. Plant Pat. No. 6,472). A large group of second generation seedlings were grown under close observation, from which the new and distinct semi-dwarf peach variety was selected for asexual propagation and commercialization.

ASEXUAL REPRODUCTION OF THE VARIETY

The present new variety of semi-dwarf peach tree was asexually reproduced by budding as performed in our experimental orchard, located near Modesto, Calif. and shows all tree and fruit characteristics come true to form and are identical to those of the original tree.

SUMMARY OF THE VARIETY

The present new variety of peach tree is semi-dwarf in size, approximately 60% of normal peach tree size, a regular and productive bearer of large size, yellow flesh, freestone peaches with good flavor and eating quality. The fruit is further characterized by having an attractive red skin color and being firm with good shipping and handling quality. The tree is further characterized by having a moderately low winter chilling requirement of approximately 450 hours, having closer leaf nodes, with larger size leaves than most standard size peach trees.

PHOTOGRAPHS OF THE VARIETY

The accompanying photographs show typical specimens of the foliage and fruit of the new peach variety with the upper and lower surface of the foliage being shown, the exterior view of the fruit and a fruit divided on its suture plane to reveal flesh coloration with the stone remaining in place. The photographs were taken shortly after being picked at maturity (firm ripe) and the colors are as nearly true as is reasonably possible in a color representation of this type.

DESCRIPTION OF THE VARIETY

The botanical description of the new and distinct variety of peach tree, its flowers, foliage and fruit are based upon observations of specimens grown at Modesto, Calif., with color terminology (except those in common terms) referenced to Reinhold Color Atlas by A. Kornerup and J. H. Wanshcer.

Tree:
- *Size.*—Semi-dwarf. Approximately 60% of regular peach tree height.
- *Vigor.*—Non-vigorous.
- *Form.*—Upright.
- *Density.*—Moderately dense.
- *Production.*—Productive.
- *Bearing.*—Regular.

Trunk:
- *Size.*—Stocky.
- *Surface.*—Shaggy-rough.
- *Color.*—Brown to grayish brown (5-D-3) to (5-D-4).

Branches:
- *Size.*—Medium — stocky.
- *Texture.*—Rough.
- *Lenticels.*—Moderate number. Large size.
- *Color.*—New growth — reddish brown to brown (6-D-8) to (7-D-8). Old growth — light brown to golden brown (5-D-7) to (5-D-8).

Leaves:
- *Size.*—Large. Average length — 7" to 7½". Average width — 1½" to 2".
- *Form.*—Lanceolate.
- *Thickness.*—Moderate to heavy.
- *Margin.*—Crenate.
- *Petiole.*—Average length — ⅞". Average width — 3/32". Longitudinally grooved.
- *Glands.*—Reniform. Average number 4, range 3 to 6. Positioned on upper portion of petiole and base of leaf blade, usually alternate.
- *Color.*—Upper surface — green to dark green (28-F-7) to (28-F-8). Lower surface — green to dull green (28-E-5) to (28-F-5).

Flower buds:
- *Size.*—Medium.

*Length.*—Medium.
*Form.*—Plump.

Flowers:
*Blooming period.*—Feb. 26, 1990 to Mar. 5, 1990. Varies slightly with climatic conditions.
*Size.*—Large — showy.
*Color.*—Pink.
*Pollen.*'—*Present.*

Fruit:
*Maturity when described.*—Firm ripe.
*Date of first picking.*—Jul. 17, 1990.
*Date of last picking.*—Jul. 23, 1990.
*Size.*—Large. Average diameter axially — $2\frac{3}{4}''$ to $3\frac{1}{8}''$. Average transversely in suture plane — $2\frac{3}{4}''$ to $3\frac{1}{8}''$.
*Form.*—Usually globose — varies from globose to slightly elongated.
*Suture.*—Distinct, shallow, nearly rounded. Extends from base to apex.
*Cavity.*—Varies from rounded to slightly elongated in suture plane. Average depth — $\frac{1}{2}''$. Average breadth — $\frac{7}{8}''$.
*Base.*—Retuse.
*Apex.*—Usually slight point. Varies from slight point to slight depression.

Skin:
*Thickness.*—Medium.
*Texture.*—Medium.
*Down.*—Moderate — short.
*Tendency to crack.*—None.
*Color.*—Yellow ground color (4-A-5) to (5-A-5). Overspread with red to lake red (9-C-8) to (9-D-8).

Flesh:
*Texture.*—Firm.
*Ripens.*—Evenly.
*Flavor.*—Mild, good balance between acid and sugar.
*Juice.*—Moderate.
*Eating quality.*—Good.

*Fibers.*—Small, tender.
*Color.*—Varies from maize yellow to dark yellow (4-A-6) to (4-A-8). Pit cavity varies from red to crayfish red (9-A-8) to (9-B-8) with red bleeding into flesh around pit cavity, usually heavier around apex of pit cavity.

Stone:
*Type.*—Freestone.
*Size.*—Medium to large. Average length — $1\frac{1}{2}''$. Average width — $1''$. Average thickness — $\frac{5}{8}''$.
*Form.*—Oval.
*Surface.*—Irregularly furrowed toward apex. pitted toward base.
*Base.*—Mostly straight, varies from rounded to straight.
*Apex.*—Acuminate.
*Sides.*—Nearly equal.
*Tendency to split.*—Slight.
*Color.*—Varies from brown to reddish brown (8-C-5) to (8-E-5).

Use: Dessert.
*Market.*—Local and long distance.
Keeping quality: Good.
Shipping quality: Good.

The present peach tree, its flowers, foliage and fruit herein described, may vary in slight detail due to climatic, soil conditions and cultural practices under which the variety may be grown; the present botanical description being of the variety grown under the ecological conditions prevailing near Modesto, Calif.

We claim:

1. A new and distinct variety of peach tree, substantially as illustrated and described, characterized by its semi-dwarf size (60% normal) and being a regular and productive bearer of large size, firm, yellow flesh, freestone fruit with good flavor and eating quality and having an attractive red skin color; the tree is further characterized by having a semi-low winter chilling requirement of approximately 450 hours.

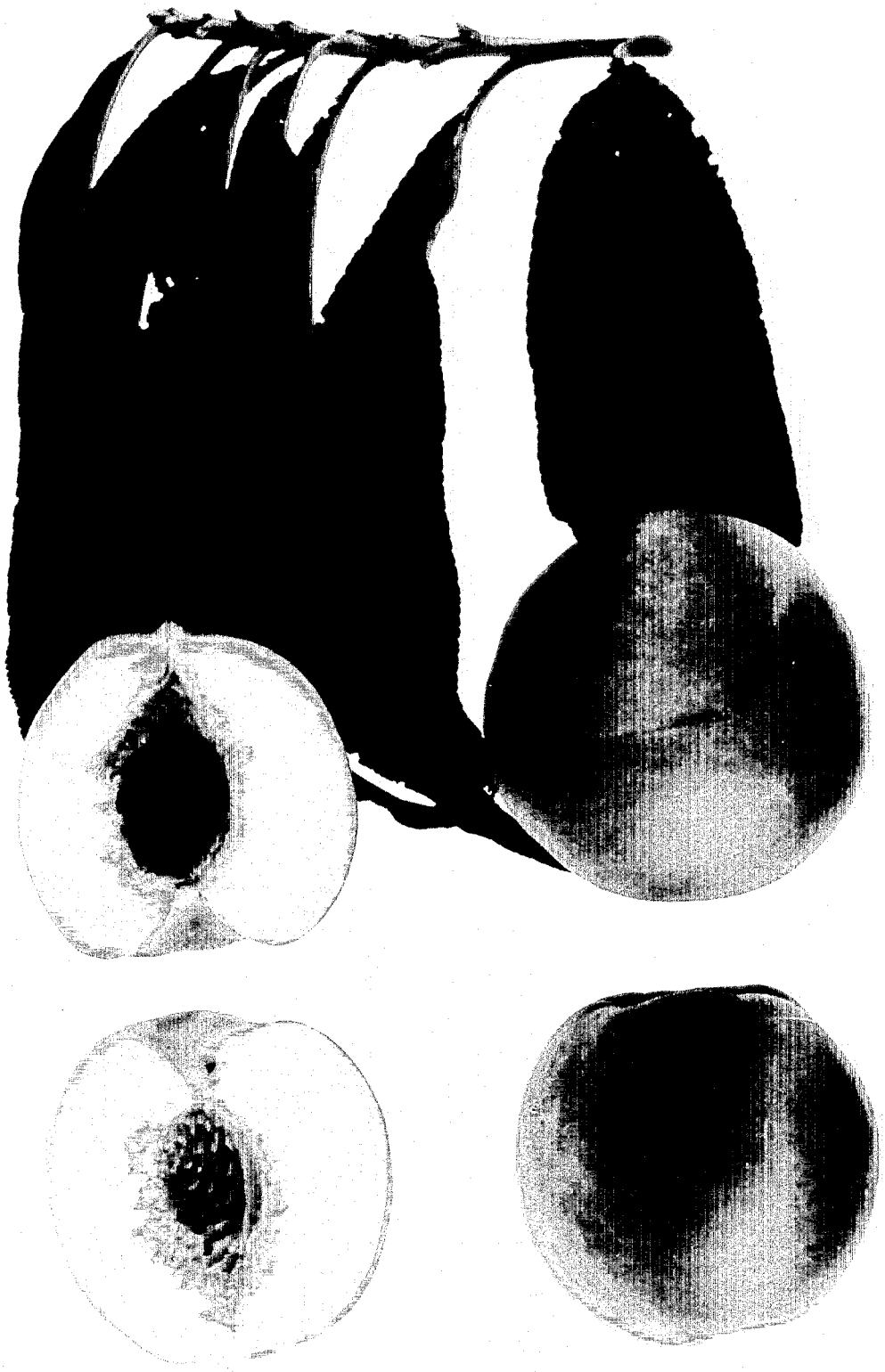

* * * * *